(12) United States Patent
Lesuisse

(10) Patent No.: US 6,365,775 B1
(45) Date of Patent: Apr. 2, 2002

(54) BIPHENYL COMPOUNDS AND THEIR USE AS OESTROGENIC AGENTS

(75) Inventor: Dominique Lesuisse, Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/627,023

(22) Filed: Jul. 27, 2000

Related U.S. Application Data

(62) Division of application No. 09/117,634, filed as application No. PCT/FR97/00184 on Jan. 30, 1997, now Pat. No. 6,147,119.

(30) Foreign Application Priority Data

Feb. 1, 1996 (FR) .............................................. 96/01212

(51) Int. Cl.$^7$ ............................................ C07C 211/03
(52) U.S. Cl. ...................... 564/337; 568/718; 568/719; 568/730
(58) Field of Search ................................ 568/718, 719, 568/730; 564/337

(56) References Cited

PUBLICATIONS

Craig et al, Australian Journal of Chemistry, vol. 9, pp 373–381, 1956.*
Selzer, Hoppe–Seyler's Zeitschrift fur physiologische Chemie, pp 39–47, 1942.*

* cited by examiner

*Primary Examiner*—Shailendra Kumar

(74) *Attorney, Agent, or Firm*—Bierman, Muserlian and Lucas

(57) ABSTRACT

Compounds of formula (I), wherein [X] represents aromatic carbocyclic rings (A) and (B), where $R_1$, $R_2$, $R_3$, $R_4$, $R_5$, $R_6$ and $R_7$ are as defined in the description, salts thereof, a method and intermediates for preparing same, the use thereof as drugs, and pharmaceutical compositions containing same, are disclosed.

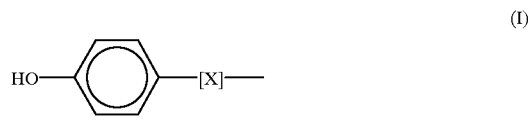

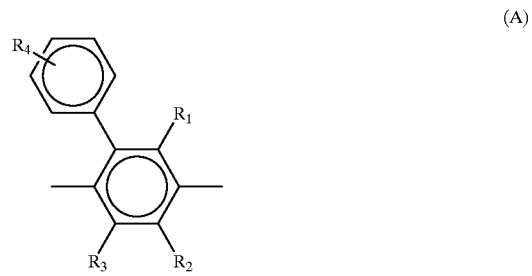

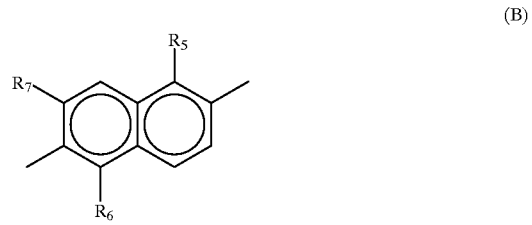

2 Claims, No Drawings

BIPHENYL COMPOUNDS AND THEIR USE AS OESTROGENIC AGENTS

PRIOR APPLICATIONS

This application is a division of U.S. patent application Ser. No. 09/117,634 filed Sep. 28, 1998, now U.S. Pat. No. 6,147,119, which is a 371 of PCT/FR97/00184 filed Jan. 30, 1997.

A subject of the invention is new biphenyl compounds, their preparation process and the intermediates of this process, their use as medicaments and the pharmaceutical compositions containing them.

A subject of the invention is the compounds of general formula (I):

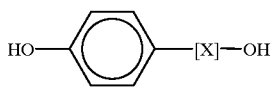

(I)

in which [X] represent the following aromatic carbocycles:

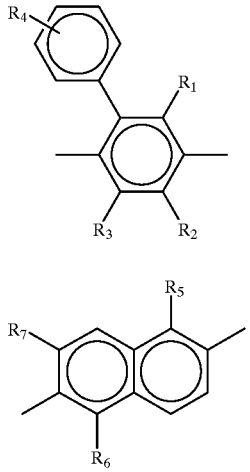

in which $R_1$ represents an alkyl radical containing from 1 to 4 carbon atoms or a hydrogen atom, $R_2$ represents an alkyl radical containing from 1 to 4 carbon atoms or a hydrogen atom, $R_3$ represents a hydrogen atom, a halogen atom, an alkyl radical containing from 1 to 4 carbon atoms or an alkoxy radical containing from 1 to 4 carbon atoms, $R_4$ in para or meta position represents a hydrogen atom, a halogen atom, a hydroxyl radical, an alkyl, alkenyl or alkynyl radical containing at most 4 carbon atoms, an alkoxy, alkylthio radical in which alkyl contains from 1 to 4 carbon atoms, an —$NR_AR_B$ group in which $R_A$ and $R_B$ identical or different represent a hydrogen atom, an alkyl radical containing from 1 to 4 carbon atoms or form together with the nitrogen to which they are linked a saturated heterocycle with 5 or 6 members optionally containing a second heteroatom chosen from nitrogen, oxygen and sulphur, their —$NR_AR_B$ group being optionally in oxidized form, a group of general formula —O—$(CH_2)_n$—$NR_AR_B$ in which n is an integer which varies from 2 to 7 and in which —$NR_AR_B$ is as defined previously, $R_5$ represents a hydrogen atom or a halogen atom, $R_6$ and $R_7$ identical or different represent a hydrogen atom, a halogen atom, an alkyl radical containing from 1 to 4 carbon atoms, or a phenyl radical optionally substituted in meta or para position by an $R_4$ radical as defined previously as well as the addition salts with acids or bases, with the exception of the compounds of formula (I) in which [X] represents the group (A) in which $R_1$, $R_2$, $R_3$ are hydrogen atoms and $R_4$ represents a hdyroxyl radical and those in which [X] represents the group (B) in which $R_5$, $R_6$ and $R_7$ are hydrogen atoms or $R_5$ and $R_6$ are hydrogen atoms and $R_7$ represents an alkyl radical containing from 1 to 4 carbon atoms.

When $R_1$, $R_2$, $R_3$, $R_4$, $R_6$, $R_7$, $R_A$ and $R_B$ represent an alkyl radical containing from 1 to 4 carbon atoms, it is a methyl, ethyl, propyl, isopropyl, butyl, isobutyl or tert-butyl radical. When $R_3$, $R_4$, $R_5$, $R_6$ and $R_7$ are halogen atoms, it is fluorine, chlorine, bromine or iodine. Preferably, it is chlorine. When $R_4$ is an alkenyl radical containing at most 4 carbon atoms, preferably it is a vinyl or propenyl radical. When $R_4$ is an alkynyl radical containing at most 4 carbon atoms, preferably it is an ethynyl or propynyl radical. When $R_3$ or $R_4$ represent an alkyloxy radical containing from 1 to 4 carbon atoms, preferably it is a methoxy, ethoxy, propyloxy, isopropyloxy or butyloxy radical. When $R_4$ is an alkylthio radical containing from 1 to 4 carbon atoms, preferably it is a methylthio, ethylthio, propylthio, isopropylthio or butylthio radical. When $R_4$ is an $NR_AR_B$ radical in which $R_A$ and $R_B$ identical or different represent a hydrogen atom or an alkyl radical containing from 1 to 4 carbon atoms, preferably it is an amino, methylamino, ethylamino, dimethylamino, diethylamino or methylethylamino radical. When $R_4$ is an —$NR_AR_B$ group in which $R_A$ and $R_B$ form with the nitrogen a saturated heterocycle, preferably it is pyrrolidino, piperidino, piperazino, morpholino or thiomorpholino groups, each of these amino groups being optionally in oxidized form.

Naturally the invention extends to the salts of the compounds de formula (I), in particular when the compounds of formula (I) contain an amino function. These are the salts formed for example with the following acids: hydrochloric, hydrobromic, nitric, sulphuric, phosphoric, acetic, formic, propionic, benzoic, maleic, fumaric, succinic, tartaric, citric, oxalic, glyoxylic, aspartic, alkanesulphonics such as methane- and ethanesulphonics, arenesulphonics, such as benzene and paratoluene sulphonics and arylcarboxylics.

These are also the salts formed under the action of a base or an alkali or alkaline-earth metal, in order to obtain for example derivatives such as sodium or potassium alcoholate or derivatives such as potassium or sodium phenolate.

A more particular subject of the invention is the compounds of general formula (I) as defined previously in which [X] is the aromatic carbocycle of general formula (A).

A more particular subject of the invention is the products of general formula (I) as defined previously in which [X] is the aromatic carbocycle of general formula (B).

A more particular subject of the invention is the products of general formula (I) as defined above, corresponding to general formula (I'):

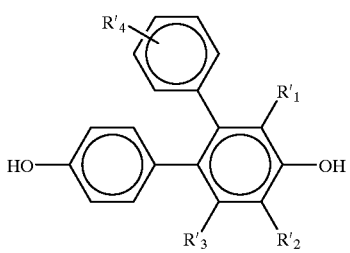

(I')

in which R'$_1$, R'$_2$ and R'$_3$ represent a hydrogen atom or an alkyl radical containing from 1 to 4 carbon atoms, R'$_4$ in meta or para position represents a hydrogen atom, a halogen atom, a hydroxyl radical, an alkyl radical, an —NR$_A$R$_B$ group or an —O—(CH$_2$)$_n$—NR$_A$RA$_B$ group, n, R$_A$ and R$_B$ being as defined previously, as well as the addition salts with acids. When R'$_4$ is an —O—(CH$_2$)$_n$—NR$_A$R$_B$ group, it is preferably the —O—(CH$_2$)$_2$—NMe$_2$ group.

A more particular subject of the invention is the products of general formula (I) as defined previously corresponding to general formula (I') in which R'$_1$, R'$_2$ and R'$_3$ are hydrogen atoms.

A quite particular subject of the invention is the compound of general formula (I) as defined previously in which R$_6$ represents a halogen atom or an —O—(CH$_2$)$_2$—N(CH$_3$)$_2$ group and R$_7$ represents a hydrogen atom.

A quite particular subject of the invention is the compound of general formula (I) as defined above the names of which follow:

5-[4-[2-(dimethylamino) ethoxy]phenyl]6-(4-hydroxyphenyl) 2-naphthalenol, 1,5-dichloro-6-(4-hydroxyphenyl)-2-naphthalenol, 5-chloro-6-(4-hydroxyphenyl)-2-naphthalenol.

A subject of the invention is also a preparation process for the products of formula (I) as defined above characterized in that a product of formula (II):

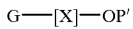

(II)

in which [X] is as defined previously, P' represents a protective group, and G represents a halogen atom or an OSO$_2$CF$_3$ group is subjected to the action, in the presence of a catalyst, of a product of formula (III):

(III)

in which Y represents a halogen atom, a B(OH)$_2$ groups or an Sn(R)$_3$ group, in which R represents an alkyl group containing from 1 to 8 carbon atoms and P represents a protective group identical to or different from P', in order to obtain a product of formula (IV):

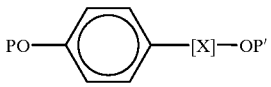

(IV)

in which P, P' and [X] have the same meaning as previously, which product of formula (IV) is subjected to one or more deprotection reactions in order to obtain the product of formula (I) as defined previously which, if appropriate is subjected to the action of an acid or base in order to obtain the corresponding salt.

The formation of the biphenyls of formula (IV) by coupling the aromatic compound of formula (II) with the aromatic compound of formula (III) is carried out in the presence of a catalyst chosen from the derivatives of palladium or in the presence of copper in the case where Y is an iodine atom and can therefore be carried out under the conditions described in the following articles:

A. Huth, I. Beetz and I. Schumann Tetrahedron (1989) 45 6679: Conditions: Na$_2$CO$_3$ 2M/Pd(Pφ$_3$)$_4$/Toluene/LiCl/EtOH/Δ)

J. K. Stille Ang. Chem. Int. Ed. (1986) 25 508: Conditions: Pd(Pφ$_3$)$_4$/LiCl/Dioxane/Δ)

T. Oh-e, N. Migawa and A. Suzuki J. Org. Chem. (1993) 58 2201–2208: Conditions: K$_3$PO$_4$/Dioxane/Δ)

P. E. Fank Chem. Rev. (1964) 38 139: Conditions: Cu/DMF/120° C. in the case where Y is an iodine atom.

E. Erdik Tetrahedron (1992) 48 9577: Conditions: nBuLi/THF/–78° C.-2) ZnCl2-3) ArBr/Pd(Pφ$_3$)$_4$/)Δ4)HCl/MeOH.

A subject of the invention is also a preparation process for products of formula (I) in which [X] is the aromatic carbocycle of formula (A) as defined above characterized in that a product de formula (V):

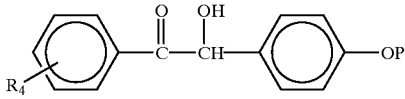

(V)

in which R$_4$ and P are as defined previously, is subjected to the action of the methylvinylketone of general formula (IV):

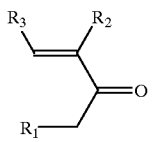

(VI)

in which R$_1$, R$_2$ and R$_3$ are as defined previously, in order to obtain the product of formula (VII):

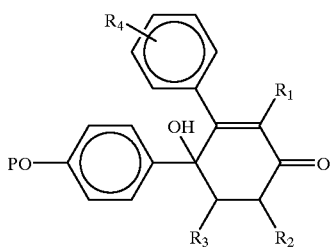

(VII)

in which $R_1$, $R_2$, $R_3$, $R_4$ and P are as defined previously, which is subjected to the action of a dehydration and aromatization reagent in order to obtain the product of formula (VIII):

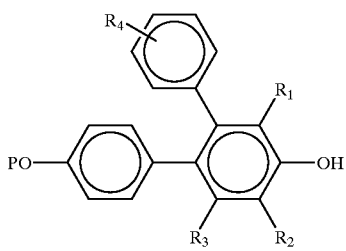

(VIII)

in which $R_1$, $R_2$, $R_3$, $R_4$ and P are as defined previously, which is subjected to the action of a deprotection reagent in order to obtain the products of formula (I) in which [X] is the aromatic carbocycle of formula (A) which, if desired, is subjected to the action of an acid in order to obtain a corresponding salt.

The protective groups P or P' are preferably chosen from an alkyl radical containing from 1 to 4 carbon atoms, a benzyl group and an $R_CR_DR_E$Si group, in which $R_C$, $R_D$ and $R_E$ identical or different represent an alkyl radical containing from 1 to 4 carbon atoms or a phenyl group. It will be quite particularly methyl, phenyl, terbutyldimethylsilyl and terbutyldiphenylsilyl radicals.

The action of the methylvinylketone of general formula (III) on the product of formula (II) is preferably carried out in the presence of a base such as potash in a dioxane/water mixture.

The dehydration and aromatization reaction is carried out for example using a mineral acid such as phosphoric acid at a temperature of 150° C. for 4 hours.

The deprotection reactions are the standard deprotection methods known to a person skilled in the art. A fairly complete list is found in the following work: Protective groups in organic synthesis T. W greene, John Wiley & Sons (1981).

By way of example, when P or P' represent a methyl radical the deprotection reaction can be carried out by the action of tribromoborane in dichloromethane or hydrochloric acid in pyridine. When P or P' represents a benzyl group a catalytic hydrogenation or a hydrolysis can be carried out with trifluoroacetic acid. When P or P' represents a silyl group the deprotection can be carried out with tetrabutylammonium fluoride (TBAF) in tetrahydrofuran (THF).

Salification by an acid or a base is carried out under standard conditions. The operation is carried out for example with hydrochloric acid, in an ethereal solution.

The compounds of formula (I) as well as their addition salts with pharmaceutically acceptable acids or bases are particularly useful products from a pharmacological point of view.

They are the original ligands of the oestrogen receptor. As such, they can be used in the treatment of disorders linked to hypofoliculinia, for example, amenorrheas, dysmenorrheas, repeated abortions, premenstrual disorders, in the treatment of certain oestrogen-dependent pathologies such as prostatic adenomas or carcinomas, mammary carcinomas and their metastases or in the treatment of benign tumors of the breast, both as an antiuterotrophic as well as in replacement treatment of symptoms linked to the menopause and in particular osteoporosis.

Therefore, a subject of the invention is, as medicaments, the products of formula (I) as described previously as well as their addition salts with pharmaceutically acceptable acids or bases.

A more particular subject of the invention is, as medicaments, the compounds of formula (I) as described previously corresponding to general formula (I') as described previously as well as the addition salts with pharmaceutically acceptable acids or bases.

A quite particular subject of the invention is, as medicaments, the following products of formula (I):
5-[4-[2-(dimethylamino) ethoxy]phenyl]6-(4-hydroxyphenyl) 2-naphthalenol,
5-chloro-6-(4-hydrophenyl)2-naphthalenol,
1,5-dichloro-6-(4-hydroxyphenyl)-2-naphthalenol.

The invention extends to the pharmaceutical compositions containing at least one medicament as defined above as active ingredient.

The compositions of formula (I) are used by digestive, parenteral or local route, for example by percutaneous route. They can be prescribed in the form of plain or sugar-coated tablets, capsules, granules, suppositories, pessaries, injectable preparations, ointments, creams, gels, microspheres, implants, patches which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The dose varies according to the illness treated and the administration route: it can be, for example, from 1 mg to 100 mg per day by oral route, for an adult.

The products of general formula (V) as defined above are obtained by the action of the product of general formula (IX):

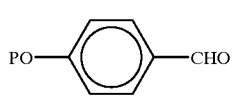

(IX)

with a product of general formula (X):

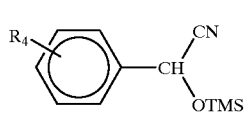

(X)

in the presence of a strong base such as LDA (lithium diisoproylamide).

This reaction is described in:
S. HUNIG et al. Chem. Ser. (1980) 113, 324–332

The products of formula (X) are obtained by the action of trimethyl silyl cyanide in the presence of a Lewis acid such as $ZnI_2$, on the corresponding aldehyde of general formula (XI):

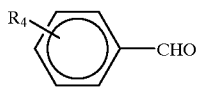

(XI)

This reaction is described in Synthesis (1980) P. 861–868. The protected products of formula (IX) are obtained from parahydroxy benzaldehyde by standard protection methods for alcohols described in the work by T. W. Greene mentioned above.

The products of formulae (II), (III), (IX), (X) and (XI) are commercial products or are easily accessible by standard functionalization methods for aromatic compounds known to a person skilled in the art.

The products of formula (VI) are also easily accessible to a person skilled in the art.

The products of formula (V) in which $R_4$ is an alkyloxy containing from 1 to 4 carbon atoms in para position and P is an alkyl containing from 1 to 4 carbon atoms, are known and are described in the following references:
Chemical Abstract: 65-10442b, 112-148858n, 59-9865f.

Finally, a subject of the invention is, as new industrial products and in particular as new intermediate products necessary for the implementation of the invention, the products of general formulae (IV), (V), (VII) and (VIII) as defined previously, with the exception of the products of formula (V) in which $R_4$ is an alkyloxy containing from 1 to 4 carbon atoms or a halogen atom and P is an alkyl radical containing from 1 to 4 carbon atoms and with the exception of the products de formulae (VII) and (VIII) in which $R_4$ is a methoxy radical, P is a methyl radical and $R_1$, $R_2$ and $R_3$ are hydrogen atoms, and with the exception of the products of formula (IV) in which P and P' are methyl or acyl radicals, X represents the group B in which $R_5$, $R_6$ and $R_7$ are hydrogen atoms.

The following examples illustrate the invention without however limiting it:

PREPARATION 1

[4-(phenylmethoxy)phenyl]-boronic acid

Stage A: 1-bromo-4-(phenylmethoxy)-benzene 15.26 g of sodium hydride at 50% in oil is added at 0° C. to a solution under inert gas of 50 g of parabromophenol in 320 ml of dimethylformamide (DMF), agitation is carried out for 30 minutes at 0° C., then 37.7 ml of benzyl bromide is added. Agitation is carried out for 2 hours 30 minutes while allowing the temperature to rise to 20° C., then the reaction mixture is poured into ice-cooled water, the precipitate is filtered, and dried, 73.35 g of expected product is obtained. Rf: 0.85 (thin layer chromatography, support: silica, eluant: cyclohexane/ethyl acetate 7/3).
I.R. spectrum: ($CHCl_3$)
Absence of OH
Aromatic 1592, 1580 and 1488 $cm^{-1}$
Stage B: [4-(phenylmethoxy)phenyl]-boronic acid 143 ml of a solution of n-Butyllithium (nBuLi) is added dropwise, under inert gas and at −78° C., to 47.08 g of the product obtained in Stage A in 375 ml of tetrahydrofuran (THF), agitation is carried out for 1 hour, then 36.5 ml of triethylborate is added. Agitation is carried out for 14 hours, while leaving the temperature to rise to 20° C., and the reaction medium is hydrolyzed using a solution of ice-cooled water containing 45 ml of concentrated sulphuric acid, for 1 hour at 20° C. The aqueous phase is extracted with ethyl acetate, the organic phases are washed with 2N soda and the aqueous phase is acidified to pH=1 using a 1N solution of hydrochloric acid in order to precipitate the boronic acid. After filtration and drying the precipitate 28.54 g of expected product is obtained.
RF: 0.16 cyclohexane/ethyl acetate 7/3)
I.R. spectrum: (Nujol)

| General absorption OH/NH region | 3650, 3615, 3510 and 3420 $cm^{-1}$ |
|---|---|
| Aromatic | 1605, 1570 and 1510 $cm^{-1}$ |
| B-O | 1410, 1340 $cm^{-1}$ |

PREPARATION 2

[4-[[(1,1-dimethylethyl)diphenylsilyl]oxy]phenyl]-boronic acid

Stage A: 1-Bromo-4-[[(1,1-dimethylethyl)diphenylsilyl]oxy)benzene 400 ml of dimethylformamide, 31.18 g of imidazole and 125.89 g of 1,1-dimethyl-ethyl-diphenyl-chlorosilane are added under an inert atmosphere and at ambient temperature to 80.89 g of parabromophenol, then the solution obtained is agitated for 2 hours. The reaction medium is poured into 2 liters of water, precipitation is observed, the solid is solubilized with ethyl acetate and the aqueous phase is extracted with ethyl acetate, the combined organic phases are dried and evaporated under reduced pressure until an oil is obtained. Pentane is added and crystallization is observed. After filtration and drying the precipitate 179.24 g of expected product is obtained. RF: 0.53 (thin layer chromatography, support: silica, eluant cyclohexane/AcOEt 95/5).

Melting point: 56° C.

NMR ($CDCl_3$, 300 MHz)

| 1.09 s | SitBu |
|---|---|
| 6.63 m | $H_3$, $H_5$ |
| 7.17 m | $H_2$, $H_6$ |
| 7.69 dd | 4H for SiΦ2 |
| 7.4 | 6H for SiΦ2 |

Stage B: [4-[[(1,1-dimethylethyl)diphenylsilyl]oxy]phenyl]boronic acid 60 ml of a solution of n-butyl-lithium is added dropwise at −78° C. and under inert gas to a solution or 30 g of the product of the preceding stage in 100 ml of anhydrous tetrahydrofuran, then after agitation for 30 minutes at −78° C., 9.95 ml of trimethylborate is added. After agitation for 2 hours 30 minutes, the bath temperature having risen to 11.9° C., 20 ml of water is added dropwise and agitation is carried out for 72 hours at ambient temperature. After evaporation of the tetrahydrofuran under reduced pressure, the aqueous phase is extracted with ether, followed by drying and concentrating under reduced pressure until an oil is obtained (26.35 g) which is purified by filtration chromatography on silica with a hexane/ethyl acetate mixture 1/1 in obtain 7.73 g of expected product in the form of the dimer.

IR (CHCl$_3$)

| O-Si | 915 and 1255 cm$^{-1}$ |
|---|---|
| B-O | 1350 and 1370 cm$^{-1}$ |
| Aromatics | 1515, 1570 and 1602 cm$^{-1}$ |

NMR (CDCl$_3$)

| 1.11 | tBu |
|---|---|
| 6.81 and 7.88 | Ph-O |
| 7.3 to 7.5 (6H) and 7.72 (4H) | PhSi |

PREPARATION 3

(4-methoxyphenyl)-boronic acid 100 ml of a solution of 10 g of p-bromoanisole in anhydrous diethyl ether is added dropwise under reflux to a suspension, under inert gas, of 1.3 g of magnesium turnings in 5 ml of anhydrous diethyl ether, and the mixture is left under reflux for 2 hours. The reaction medium is the poured into a solution of 9.02 ml of triethylborate in 60 ml of anhydrous ether cooled down to −70° C. After agitation for 1 hour at −70° C., then for 1 hour at ambient temperature, the solution is poured into a mixture containing 11 ml of sulphuric acid and 50 g of ice and water and agitation is carried out for 1 hour. The organic phase is extracted with 100 ml of a saturated aqueous solution of sodium bicarbonate, the aqueous phases are combined, reacidified with 6N hydrochloric acid, extracted with ether, dried and evaporated under reduced pressure, 3.9 g of expected product is obtained.

I.R. spectrum: (Nujol)

Complex absorption OH/NH region, 1609, 1573 and 1518 cm$^{-1}$

NMR (DMSO-d6, 300 MHz)

| 3.76 s | OCH$_3$ |
|---|---|
| 6.88 d J = 9 Hz | H$_3$ and H$_5$ |
| 7.78 d J = 9 Hz | H$_2$ and H$_6$ |
| 7.86 | B(OH)$_2$ |

PREPARATION 4

4-(dimethylaminoethoxy) phenyl boronate.

2.5 g of 1-bromo 4-(dimethylamino) ethoxy benzene described in the Patent RO 83118 in 50 ml of tetrahydrofuran is cooled down to −78° C. then 7.86 ml of n-butyllithium is added over 5 minutes. Agitation is carried out for 30 minutes at −78° C., 1.35 ml of trimethyl borate is added over 10 minutes, the reaction medium is maintained for 2 hours under agitation at −78° C. then for 3 hours at ambient temperature. 3 ml of water is added dropwise and agitation is carried out for 72 hours at ambient temperature. The solvent is evaporated off under reduced pressure, the residue is chromatographed on silica (eluant THF) then on neutral alumina (eluant: CH$_2$Cl$_2$ then CH$_2$Cl$_2$-MeOH 95-5). 810 mg of expected product is obtained.

Rf=0.2 (CH$_2$Cl$_2$-MeOH 95-5).

EXAMPLE 1

5-[-4-[2-(dimethylamino)ethoxy]phenyl]6-(4-hydroxyphenyl) 2-naphthalenol.

Stage A: 1-[4-[2-(dimethylamino)ethoooxy]phenyl]6-methoxy2-naphthalenol.

a) 1-bromo 6-methoxy 2-naphthalenol.

1.05 g of 6-methoxy 2-naphthalenol prepared as in Example 2 Stage A in 15 ml of ethanol, 0.84 g of N-bromoacetamide is added and agitation is carried out for 1 hour at ambient temperature. The reaction medium is poured into 800 ml of water followed by extraction with methylene chloride, drying, the solvent is evaporated off under reduced pressure, the residue is purified by chromatography on silica (eluant; cyclohexane-dichloromethane 50-50). 0.75 g of expected product is collected.

b) 2.5 g of the product obtained as in Stage a) with 2,45 g of 4-(dimethylaminoethoxy) phenyl boronate prepared as indicated in Preparation 4 in 150 ml of dioxane is agitated under reflux for 3 hours in the presence of 0.85 g of palladium tetrakis and 3.8 g of potassium phosphate monohydrate. The solvent is evaporated off under reduced pressure, the residue is chromatographed on silica (eluant: dichloromethane-methanol 95-5) and 1.8 g of expected product is obtained.

Stage B: 1-[4-(2-dimethylamino) ethoxy]phenyl]6-methoxy 2-naphthalenol trifluoromethanesulphonate.

1 g of the product obtained in Stage A is mixed with 30 ml of pyridine then 1.25 ml triflic anhydride is added. The reaction medium is heated for 3 hours at 80°–90° C., then poured into a saturated aqueous solution of sodium biocarbonate. Extraction is carried out with ethyl acetate, followed by drying, the solvent is evaporated off under reduced pressure, the residue is chromatographed on silica (eluant: cyclohexane-ethyl acetate 7-3 then dichloromethane-methanol 95-5). 0.72 g of expected product is obtained.

Rf=0.3 (eluant: CH$_2$Cl$_2$—CH$_3$OH 95-5).

Stage C: N,N-diemthyl 2-[4-[6-methoxy 2-(4-methoxyphenyl) 1-naphthalenyl]phenoxyl]ethanamine.

0.64 g of the triflate obtained in Stage B with 274 mg of 4-methoxyphenyl boronic acid prepared as indicated in Preparation 3 in 30 ml of dimethylformamide is heated for 3 hours at 120° C. in the presence of 32 mg of dipalladium tris(dibenzylideneacetone), 505 mg of potassium phosphate monohydrate, 177 mg of potassium bromide and 73 mg of triphenylphosphine. The solvent is evaporated off under reduced pressure, the residue is chromatographed on silica (eluant: dichloromethane-methanol 95-5 then ethyl acetate-acetone-methanol 80-10-10). 0.28 g of expected product is obtained.

RF=0.16(AcOEt—(CH$_3$)$_2$CO—CH$_3$OH 80-10-10).

IR spectrum (CHCl$_3$)

aromatic: 1625, 1610, 1600, 1572, 1515, 1499 cm$^{-1}$.

Stage D: 5-[-4-[2-(dimethylamino) ethoxy]phenyl]6-(4-hydroxyphenol) 2-naphthalenol.

95 mg of the product obtained as in Stage C is heated for 1 hour at 200° C. with 1.2 g of pyridinium hydrochloride, followed by taking up in a saturated aqueous solution of sodium bicarbonate, extraction with ethyl acetate and drying, the solvent is evaporated off under reduced pressure, the residue is chromatographed on silica (eluant: dichloromethane-methanol 90-10) and 35 mg of expected product is obtained.

Rf=0.07 (AcOEt —(CH$_3$)$_2$-CO—CH$_3$OH 80-10-10).

IR spectrum (Nujol)

aromatic: 1620, 1608, 1508 cm$^{-1}$

EXAMPLE 2

5-chloro-6-(4-hydroxyphenyl)-2-naphthalenol

Stage A: protection of the naphthol 2-hydroxy-6-methoxy-naphthalene 3.75 ml of methyl sulphate and 0.8 g of soda are added, under an inert atmosphere to 3.2 g of 2,6-dihydroxynaphthalene in 20 ml of methanol and 3 ml of water, and the reaction medium is heated for 15 hours at 40° C. After having poured the reaction medium into 200 ml of water, extraction is carried out with ethyl acetate, followed by drying, filtering and evaporating under reduced pressure. The crude product is purified by chromatography and 1.2 g of expected product is obtained as well as 1.6 g of biprotected analogue.

Rf=0.24 (cyclohexane/ethyl acetate 80/20) NMR (CDCl$_3$)

| 3.90 (s) | OCH$_3$ |
|---|---|
| 4.89 (ws) | OH |
| 7.58 d; 7.64 d | H$_4$; H$_8$ |
| 7.03 to 7.15 m 4H | H$_1$, H$_3$, H$_5$, H$_7$ |

Stage B: Chlorination 1-chloro-2-hydroxy-6-methoxy-naphthalene 175 mg of the product prepared in the preceding stage is added under an inert atmosphere to a solution of thionyl chloride in 5 ml of chloroform at ambient temperature and agitation is carried out for 1 hour. After washing with water, drying, filtration and evaporation under reduced pressure, 200 mg of expected product is obtained.

Rf=0.25 (cyclohexane/ethyl acetate 70/30)

NMR (CDCl$_3$)

| 3.91 s | OCH$_3$ |
|---|---|
| 5.71 s | OH |
| 7.59 d; 7.97 d | H$_4$; H$_8$ |
| 7.23 m | H$_3$ |
| 7.11 d J = 2, 5 Hz | H$_5$ |
| 7.23 m | H$_7$ |

Stage C: formation of the triflate 1-chloro-2-trifluoromethylsulphonyloxy-6-methoxy-naphthalene 0.75 ml of triflic anhydride is added at 0° C. to a solution, under an inert atmosphere of 600 mg of the chloronaphthol obtained in the preceding stage in 50 ml of pyridine, and agitation is carried out for 1.5 hours at ambient temperature. The reaction medium is then poured into 300 ml of water, followed by extraction with ethyl acetate, drying, filtering then evaporation under reduced pressure. 1 g of expected product is obtained which used as it is in the following stage.

Rf=0.28 (cyclohexane/ethyl acetate 70/30)

Stage D: Coupling 1-chloro-2-(4-[[(1,1-dimethylethyl)diphenylsilyl]oxy]phenyl)-6-methoxy-naphthalene A mixture constituted by 1 g of the triflate prepared in the preceding stage, 1.5 g of the boronic acid obtained in Preparation 2, 420 mg of potassium bromide, 1.1 g of potassium phosphate monohydrate, 100 mg of palladium tetrakis and 50 ml of dioxane are mixed together for 8 hours, under an inert atmosphere, under reflux. After washing with water, drying, filtration then evaporation under reduced pressure, the crude product is purified by chromatography eluting with a cyclohexane/ethyl acetate mixture 97/3. 1.4 g of expected product is obtained.

Rf=0.55 (cyclohexane/ethyl acetate 90/10)

Stage E: Deprotection (desilylation)

1-chloro-2-(4-hydroxyphenyl)-6-methoxy-naphthalene 700 mg of the product obtained in the preceding stage in 50 ml of tetrahydrofuran and 1.5 ml of tetrabutylammonium fluoride (1M/THF) are agitated for 30 minutes, under an inert atmosphere and at ambient temperature. After evaporation under reduced pressure, the crude product is purified by chromatography eluting with a cyclohexane/ethyl acetate mixture 90/10. 300 mg of expected product is obtained.

Rf=0.45 (cyclohexane/ethyl acetate 70/30) NMR (CDCl$_3$)

| 3.95 s | OCH$_3$ |
|---|---|
| 4.84 ml | OH |
| 7.16 d | H$_5$ |
| 7.29 dd | H$_7$ |
| 7.40 d, 7.68 dd, 8.29 d | H$_3$, H$_4$, H$_8$ |
| 6.93; 7.40 | H of Ph-OH |

Stage F: Deprotection: demethylation 5-chloro-6-(4-hydroxphenyl)-2-naphthalenol 300 mg of the product obtained in the preceding stage and 3 g of pyridinium hydrochloride are mixed together under an inert atmosphere and the reaction medium is heated for 2 hours at 200° C. After having poured the reaction medium into 30 ml of water, extraction is carried out with ethyl acetate, followed by washing with water, drying, filtering and evaporation under reduced pressure. The crude product is purified by chromatography eluting with a dichloromethane/ether mixture 95/5. 120 mg of pure expected product is obtained.

Rf=0.20 (cyclohexane/ethyl acetate 70/30) M.p.=254° C. NMR (CDCl$_3$)

| 7.20 to 7.40 m, 7.71 dl, 8.13 dl | H of naphthyl |
|---|---|
| 6.87; 7.30 | H of Ph-OH |
| 9.57 s; 10.00 s | OH (Ph-O<u>H</u>, Naphth-O<u>H</u>) |

EXAMPLE 3

1,5-dichloro-6-(4-hydroxyphenyl)-2-naphthalenol

The operation is carried out in a similar manner to Example 2 starting with 100 mg of 1,5-dichloro-2-hydroxy-6-methoxy-naphthalene (obtained by the action of 0.35 ml of sulphuryl chloride on 350 mg of the product of Example 2 Stage A in 20 ml of dichloromethane with a yield of 100%) and by using the boronic acid of Preparation 1, 15 mg of pure expected product is obtained.

Rf=0.60 (cyclohexane/ethyl acetate 50/50) NMR (CDCl$_3$)

| | |
|---|---|
| 7.40; 7.53 d; 8.04 d; 8.30 d | H of naphthyl |
| 6.94; 7.430 | H of Ph-OH |
| 4.85 wm; 5.92 wm | (Ph-O$\underline{H}$, Naphth-O$\underline{H}$) |

PHARMACOLOGICAL COMPOSITION

Tablets were prepared corresponding to the following general formula:

| | |
|---|---|
| -product of Example 2 | 50 mg |
| -Excipient (talc, starch, magnesium stearate) qs for a tablet completed at | 120 mg |

PHARMACOLOGICAL STUDY OF THE PRODUCTS OF THE INVENTION

Human oestrogen receptor (HOR)

A cytosolic extract of SF9 cells containing the recombinant human oestrogen receptor is obtained by overexpression in an insect-Baculovirus cell system, according to the general methodology described by N. R. WEBB et al. (Journal of Methods in Cell and Molecular Biology, (1990) Vol. 2 No. 4, 173–188) and the application of which is described for the expression of human hormonal receptors, for example the human glucocorticoid receptor (G. SRINIVASAN et al. Molecular Endocrinology (1990) vol 4 No. 2 209–216).

The BaculoGold Transfection Kit (PharMingen, reference 21000K) is used to generate the recombinant baculovirus containing the cDNA fragment described in the expression vector HEGO by L. TORA et al. (The EMBO Journal (1989) vol. 8 No. 7 1981–1986), containing the region coding for the wild-type human oestrogen receptor with a glycine in position 400.

The recombinant virus thus obtained is used to express the oestrogen receptor in the SF9 insect cells (ATCC CRL1711), according to the known methodology mentioned previously.

$2*10^7$ SF9 cells are cultured in a 175 cm$^2$ "Falcon" flask in the TNM-FM "SIGMA" medium supplemented by 10% of foetal calf serum (FCS) and by 50 microgram/ml of gentamycin. After infection then incubation at 27° C. for 40 to 42 hours, the cells are lysed in 1 ml of lysis buffer (Tris 20 mM-HCl pH8, EDTA 0.5 mM, DTT 2 mM, Glycerol 20%, KCl 400 mM) with a freezing-thawing cycle which is repeated another two times. The supernatant, containing the recombinant human oestrogen receptor is kept in liquid nitrogen by 0.5 ml doses.

The supernatant is incubated at 0° C. for 24 hours with a constant concentration (T) of tritiated oestradiol in the presence of increasing concentrations of either unlabelled oestradiol (0–1000×10$^{-9}$M), or of unlabelled product to be tested (0–25000×10$^{-9}$M). The concentration of bound tritiated oestradial (B) is then measured in each incubate by the technique of adsorption with carbon dextran.

Calculation of the relative bond affinity (RBA):

The following two curves are drawn: the percentage of bound tritiated hormone 100×B/B0 as a function of the logarithm of the concentration of unlabelled reference hormone or as a function of the concentration of unlabelled test product.

The straight line of the equation $$I_{50}=(B0/B0+B\ min)/2=100\ (1+Bmin/B0)=50\ (1+Bmin/B0)$$

is determined.

B0=concentration of bound tritiated hormone in the absence of any unlabelled product.

B=concentration of bound tritiated hormone in the presence of a concentration X of the unlabelled product.

B min=concentration of bound tritiated hormone for an incubation of this tritiated hormone at a concentration (T) in the presence of a large excess of unlabelled reference hormone (1000×10$^{-9}$M) for the human receptor.

The intersections of the straight line $I_{50}$ and the curves allow the evaluation of the concentrations of unlabelled reference hormone (CH) and of the unlabelled test product (CX) which inhibit by 50% the binding of the tritiated hormone on the receptor.

The relative bond affinity (RBA) of the test product is calculated by the equation: RBA=100 (CH)/(CX).

The results obtained are as follows:

| Examples | HOR oestradiol = 100 24 hours |
|---|---|
| 1 | 28 |
| 2 | 49 |
| 3 | 5 |

Conclusion:

While these products have an affinity which is 2 to 20 times weaker than that of oestradiol, the fixation on the oestrogen receptor is a new fact for this family of products.

What is claimed is:

1. A compound having a formula selected from the groups consisting of

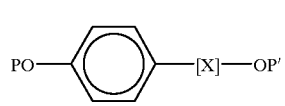

IV

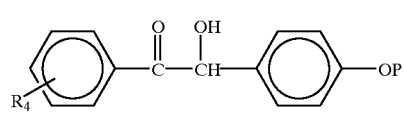

V

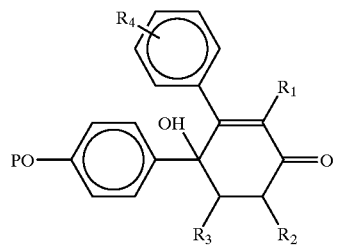

VII

-continued

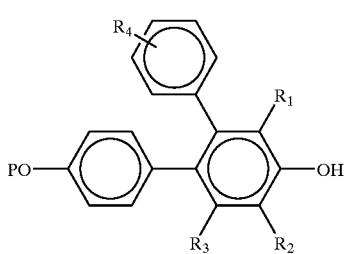

wherein X is

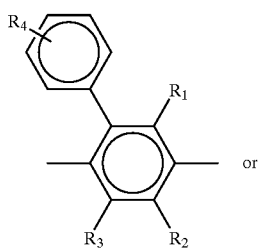  or

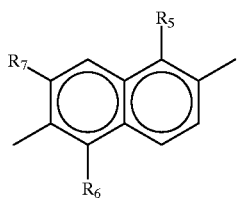

$R_1$ and $R_2$ are individually hydrogen or alkyl of 1 to 4 carbon atoms, $R_3$ is selected from the group consisting of hydrogen, halogen, alkyl of 1 to 4 carbon atoms and alkoxy of 1 to 4 carbon atoms, $R_4$ is in the para or meta position and is selected from the group consisting of hydrogen, halogen, —OH, optionally oxidized

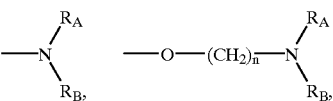

and alkyl, alkenyl, alkynyl, alkenyl, alkynyl, alkylthio and alkoxy, all up to 4 carbon atoms, $R_A$ and $R_B$ are individually hydrogen or alkyl of 1 to 4 carbon atoms or taken together with the nitrogen form a saturated heterocycle of 5 to 6 ring members optionally containing a second heteroatom selected from the group consisting of nitrogen, oxygen and sulfur, n is an integer of 2 to 7, $R_5$ is hydrogen or halogen, $R_6$ and $R_7$ are individually selected from the group consisting of hydrogen, halogen, alkyl of 1 to 4 carbon atoms and phenyl unsubstituted or substituted with $R_4$ as defined above and P and P' are —OH protective groups with exception of compounds of formula V wherein $R_4$ is alkoxy of 1 to 4 carbon atoms or halogen and P is alkyl of 1 to 4 carbon atoms and with exception of compounds of formulas VII and VIII wherein $R_4$ is methoxy, P is methyl and $R_1$, $R_2$ and $R_3$ are hydrogen and with exception of compounds of formula IV wherein P and P' are methyl or acyl and X is B in which $R_5$, $R_6$ and $R_7$ are hydrogen.

2. A compound of claim 1 wherein X is

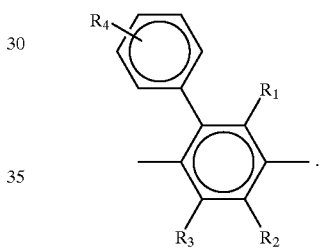

* * * * *